US011311406B2

(12) United States Patent
Roszkowiak et al.

(10) Patent No.: US 11,311,406 B2
(45) Date of Patent: Apr. 26, 2022

(54) EXTERNAL FECAL MANAGEMENT DEVICE

(71) Applicant: Medline Industries, LP, Northfield, IL (US)

(72) Inventors: Amanda Roszkowiak, Schaumburg, IL (US); Derrick Roemisch, McHenry, IL (US); Michael V. Turturro, Arlington Heights, IL (US); Morgan Uridil, Evanston, IL (US)

(73) Assignee: Medline Industries, LP, Northfield, IL (US)

( * ) Notice: Subject to any disclaimer, the term of this patent is extended or adjusted under 35 U.S.C. 154(b) by 770 days.

(21) Appl. No.: 16/178,087

(22) Filed: Nov. 1, 2018

(65) Prior Publication Data
US 2020/0138618 A1 May 7, 2020

(51) Int. Cl.
*A61F 5/451* (2006.01)
*A61F 5/443* (2006.01)
*A61F 5/441* (2006.01)
*A61F 5/44* (2006.01)

(52) U.S. Cl.
CPC ............. *A61F 5/443* (2013.01); *A61F 5/441* (2013.01); *A61F 5/4405* (2013.01); *A61F 5/451* (2013.01)

(58) Field of Classification Search
CPC .... A61F 5/44–442; A61F 5/443; A61F 5/451; A61F 5/455; A61F 5/453
See application file for complete search history.

(56) References Cited

U.S. PATENT DOCUMENTS

| 4,030,500 | A | | 6/1977 | Ronnquist |
| 4,182,332 | A | | 1/1980 | Delaney |
| 4,445,898 | A | | 5/1984 | Jensen |
| 4,471,782 | A | | 9/1984 | Shuffield |
| 4,496,356 | A | | 1/1985 | Lognion |
| 4,534,768 | A | * | 8/1985 | Osburn ................ A61F 5/453 600/573 |
| 4,772,260 | A | | 9/1988 | Heyden |
| 4,784,656 | A | | 11/1988 | Christian |
| 5,509,893 | A | | 4/1996 | Pracas |
| 5,520,669 | A | | 5/1996 | Mulholland |
| 5,714,225 | A | * | 2/1998 | Hansen ................ A61F 5/443 428/114 |

(Continued)

FOREIGN PATENT DOCUMENTS

JP  2001000536  1/2001
WO  2008048856  4/2008

*Primary Examiner* — Susan S Su
(74) *Attorney, Agent, or Firm* — Fitch, Even, Tabin & Flannery LLP

(57) ABSTRACT

A fecal management device, and methods for applying a fecal management device to a patient, are described herein. In some embodiments, the fecal management device comprises a sheath having a first end and a second end, a first connector at the first end of the sheath, said first connector comprising a substrate that includes a first adhesive and a second adhesive, the second adhesive disposed relatively outwardly with respect to the first adhesive, the substrate having a multi-lobed contour with two opposing concave regions, a sheath port located at the second end of the sheath, the sheath port configured to removably mate with a collection bag port, and a collection bag, wherein the collection bag includes the collection bag port.

19 Claims, 10 Drawing Sheets

(56) References Cited

U.S. PATENT DOCUMENTS

| | | | |
|---|---|---|---|
| 5,741,239 A | 4/1998 | Mulholland | |
| 5,827,247 A * | 10/1998 | Kay | C08L 1/28 |
| | | | 604/327 |
| 8,840,594 B2 | 9/2014 | Sharma | |
| 9,452,080 B2 | 9/2016 | Holzbauer | |
| 9,463,110 B2 | 10/2016 | Nishtala | |
| 2009/0062755 A1 * | 3/2009 | Burgess | A61F 5/455 |
| | | | 604/326 |
| 2011/0282311 A1 * | 11/2011 | Nishtala | A61M 1/69 |
| | | | 604/332 |
| 2012/0116336 A1 | 5/2012 | Sharma | |
| 2014/0323909 A1 * | 10/2014 | Kim | A61B 5/4255 |
| | | | 600/562 |
| 2015/0011955 A1 | 1/2015 | Sharma | |
| 2017/0312116 A1 * | 11/2017 | Laniado | A61F 5/443 |
| 2020/0138620 A1 * | 5/2020 | Schwab | A61F 5/4556 |
| 2020/0188160 A1 * | 6/2020 | Udayakumar | A61F 5/443 |

\* cited by examiner

EXTERNAL FECAL MANAGEMENT DEVICE

TECHNICAL FIELD

This application relates generally to medical devices and, more particularly, to fecal management devices.

BACKGROUND

Many challenges exist surrounding the care of patients that are incontinent, bedridden, or otherwise unable to care for themselves. Management of waste produced by patients poses unique challenges. For example, the waste of a bedridden patient must be kept away from the patient for reasons of sanitation and to reduce the occurrence of sores and infection. Many fecal management systems include a sheath and associated collection bag. When the collection bag becomes full, the entire fecal management system must be removed from the patient. This can cause pain, discomfort, or injury to the patient and can be inconvenient for the caregiver. Some prior art fecal management devices are fastened to the patient with adhesive. Some such devices are prone to leakage and are often uncomfortable for the patient as their geometry is not well suited to the patient's anatomy.

Described herein are fecal management devices and methods that seek to minimize, if not overcome, the disadvantages of the above-described existing fecal management systems. In some embodiments, the fecal management devices include a quick connect design that enables a collection bag to be quickly and easily removed from the fecal management device. Additionally, in some embodiments, fecal management devices include a substrate applied to a substrate that is shaped to securely and comfortably adhere the fecal management devices to the patient. The external configuration of the substrate may have opposing first and second convex lobes and opposing first and second concave lobes.

BRIEF DESCRIPTION OF THE DRAWINGS

Embodiments of the inventive subject matter are illustrated in the figures of the accompanying drawings in which.

DETAILED DESCRIPTION

Figure 1:
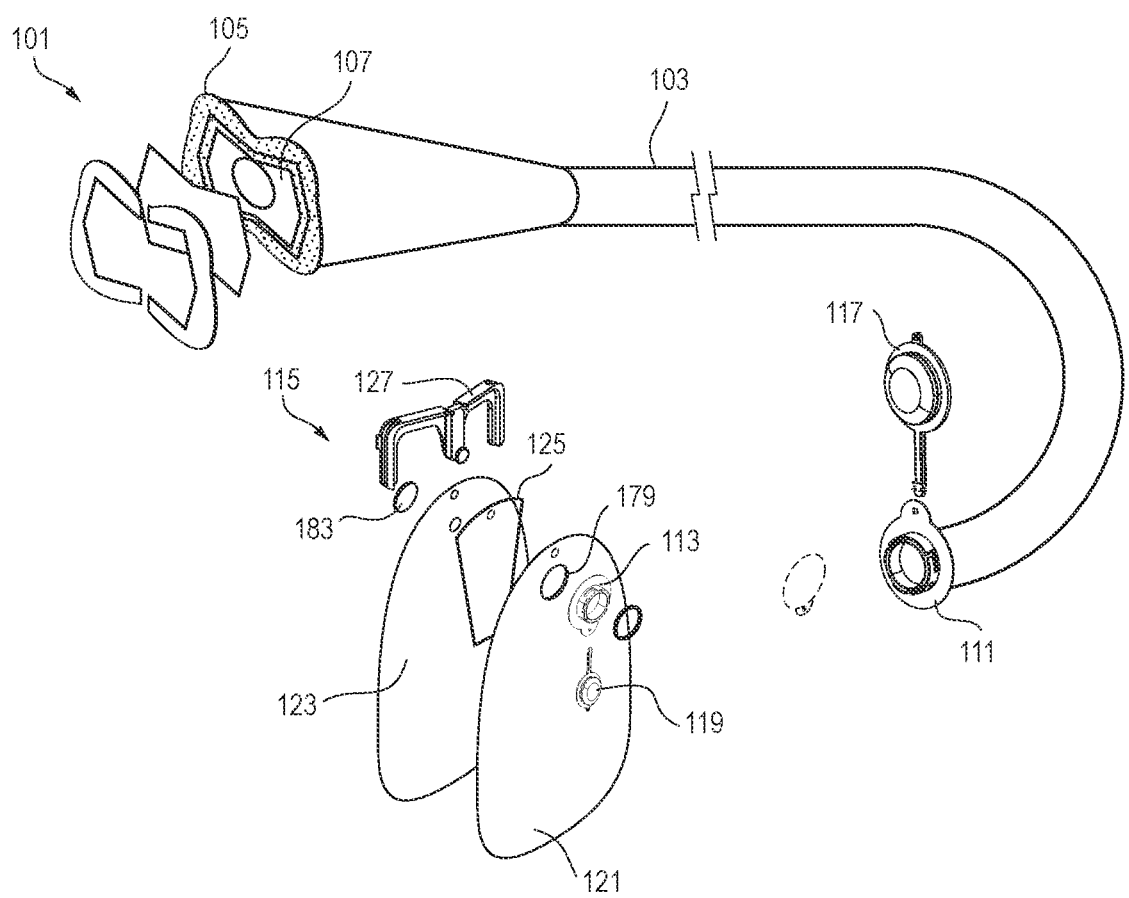
FIG. 1 is a representational view illustrating various components of a fecal management device.
Figure 3:
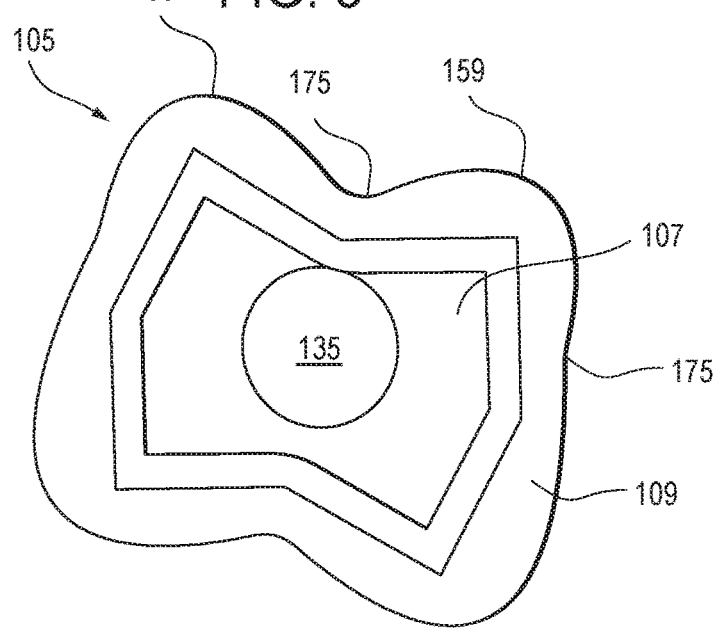
FIG. 3 is a plan view of the substrate illustrated in FIG. 2.

With reference to FIG. 1, the illustrated fecal management device 101 includes a sheath 103 having a first end (proximal to the patient) and a second end (distal from the patient). Affixed to the first end of the sheath 103 is an adhesive substrate 105 that is designed for connection to the rectum of a patient. The substrate includes a first adhesive 107 and a second adhesive 109 (FIG. 3). Though not shown in FIG. 1, the first end of the sheath 103 can include an intrarectal catheter for the collection of fecal matter from the patient.

The second end of the sheath 103 includes a sheath port 111. The sheath port 111 is configured to mate with a collection bag port 113 of a collection bag 115. The connection between the sheath port 111 and the collection bag port 113 allows the collection bag 115 to be removed from the sheath 103. Because the collection bag 115 can be removed from the sheath 103, the fecal management device 101 can continue to be used after the collection bag 115 is removed and replaced with another collection bag. Because the sheath 103 can remain in place during replacement of the collection bag 115, portions of the fecal management device 101 that are attached to the patient can remain in place decreasing discomfort and incidence of injury for the patient.

The sheath port 111 and the collection bag 115 can include optional caps such as the sheath port cap 117 and the collection bag port cap 119. The sheath port cap 117 and the collection bag port cap 119 are configured to mate with the sheath port 111 and the collection bag port 113, respectively. The sheath port cap 117 and the collection bag port cap 119 prevent unwanted egress of fecal matter from the sheath 103 and the collection bag 115, respectively, when the collection bag 115 is removed from the sheath 103.

The sheath 103 acts a conduit to allow the flow of fecal matter from the patient to the collection bag 115. Accordingly, the sheath 103 can take any suitable form (e.g., rigid, flexible, and/or collapsible tubing). The sheath may for example take the form of a clear or translucent plastic film.

The exemplary collection bag 115 depicted in FIG. 1 comprises two sections: a first section 121 and a second section 123. The first section 121 and the second section 123 comprise fluid-impermeable plastic and are affixed to one another (e.g., via heat sealing). The example collection bag 115 depicted in FIG. 1 includes an anti-reflux device 125, a dual hanger 127, and a filtering device affixed to a filter port 131. The anti-reflux device 125 inhibits the unwanted egress of fecal matter from the collection bag 115 if the collection bag 115 is rotated (e.g., held or placed upside-down).

The dual hanger 127 (discussed in more detail with respect to FIGS. 10 and 11) is configured to allow the collection bag 115 to be hung from either a bed frame or a flat metal surface as is sometimes found in caregiver settings. The filter port 131 allows gas to escape from the collection bag 115 to prevent inflation of the collection bag 115. The filter port 131 includes the filtering device 183 to diminish odor emanating from the collection bag 115 via the filter port 131.

The substrate 105 is affixed to the sheath 103. The substrate 105 adheres the fecal management device to the patient. In some embodiments, the substrate 105 is configured to adhere the fecal management device to the patient for long periods of time (e.g., one week or longer).

With reference to FIG. 3, the substrate 105 comprises a first adhesive 107 and a second adhesive 109 and an aperture 135. The aperture 135 allows fecal matter to flow from the patient to the sheath. The second adhesive 109 is disposed relatively outwardly with respect to the first adhesive 107. In some embodiments, the first adhesive 107 is located centrally within the second adhesive 109. The first adhesive 107 can be centrally located within the second adhesive 109 in any suitable manner. For example, the second adhesive 109 can be a contiguous adhesive and the first adhesive 107 can be placed on the second adhesive 109. Alternatively, the second adhesive 109 may only include adhesive on the portion of the second adhesive 109 that is not covered by the first adhesive 107, but nonetheless be a solid surface.

In some embodiments, the first adhesive 107 is suited for contact with sensitive areas of the patient. In such embodiments, the first adhesive 107 can comprise, for example, a hydrocolloid adhesive. The second adhesive 109 can be a resilient adhesive suitable for firm adhesion to the patient. For example, the second adhesive 109 can comprise any adhesive suitable for binding to a nonwoven substrate. It is believed that the hydrocolloid adhesive will contact sensitive areas of the patient's buttocks and rectum and that the use of such adhesive will minimize skin irritation and damage.

Figure 2:
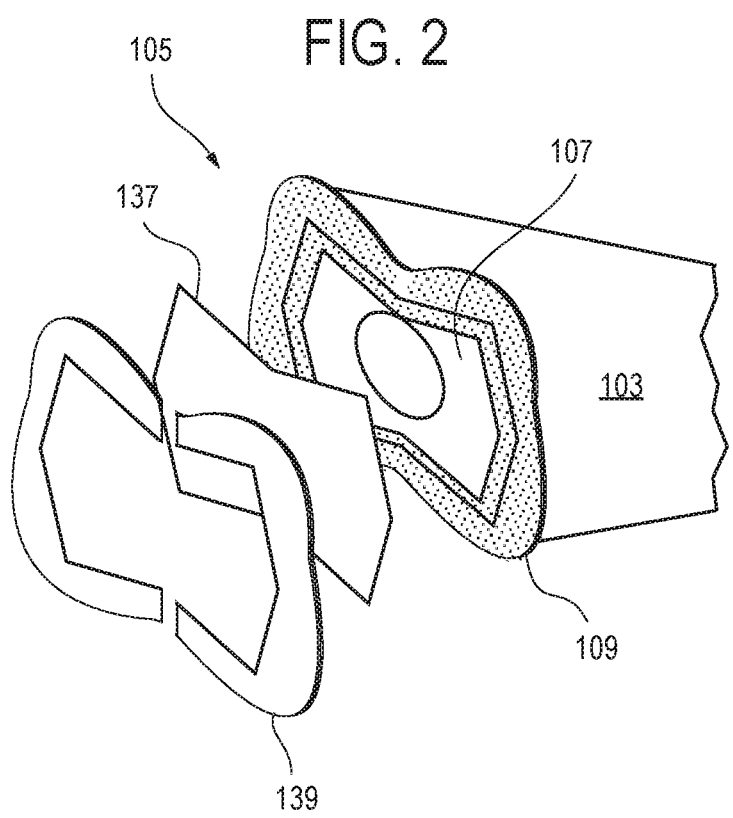
FIG. 2 is a perspective view of a substrate of the fecal management device illustrated in FIG. 1.

The substrate 105 includes a protective backing layer that is configured to protect the substrate 105 and prevent the substrate 105 from adhering to unwanted surfaces before application. As depicted in FIG. 2, the first adhesive 107 includes a first protective layer 137 and the second adhesive 109 includes a second protective layer 139. The protective layer is removed to expose the adhesive portion of the substrate 105. Accordingly, the protective layer is removed before and/or during adhesion of the substrate 105 to the patient.

The first adhesive 107 may take the shape of a space-filling polygon, i.e. it may have a space-filling polygonal shape. For example, in some embodiments, the space-saving polygonal shape can be a tessellating shape. The space-filling polygonal shape depicted in FIG. 3 is a "bowtie" shape. This "bowtie" shape is well-adapted to conform to the patient's body. In some embodiments, the first adhesive is disposed on a secondary substrate. In such embodiments, the shape of the secondary substrate can complement the space-filling polygonal shape. For example, the shape of the second substrate can match that of the first adhesive 107, whether or not the same size.

The substrate 105 has a multi-lobed contour, somewhat bearing a general resemblance to a butterfly. The multi-lobed contour includes two lobes 159 forming two opposing concave regions 175. Like the "bowtie" shape of the first adhesive 107, the multi-lobed shape of the second adhesive 109 is well adapted to conform to the patient's body.

Figure 5:
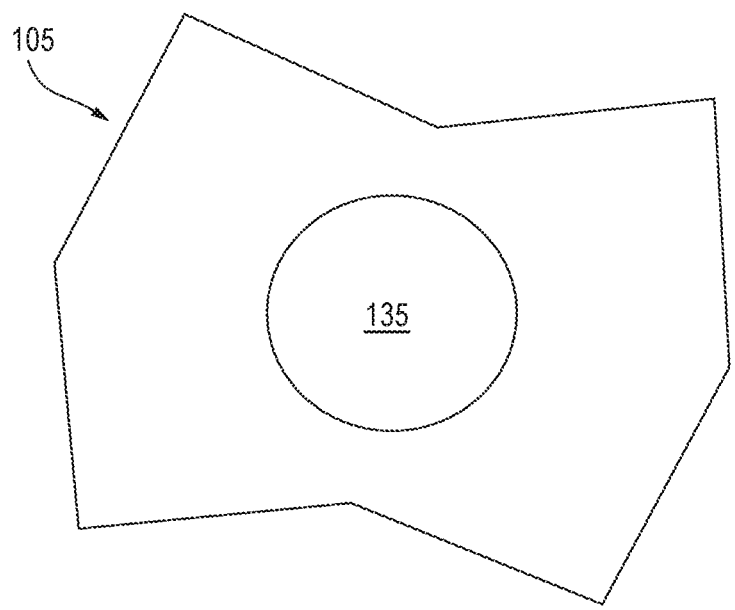
FIG. 5 is an alternate substrate 105 including a single adhesive.

In some embodiments, the substrate 105 may comprise only a single adhesive, such as a hydrocolloid adhesive. Such a substrate 105 is depicted in FIG. 5. Although the substrate 105 includes only a single adhesive, the substrate 105 still includes an aperture 135. The substrate 105 can take the shape of the "bowtie" multi-lobed contour.

Figure 4:
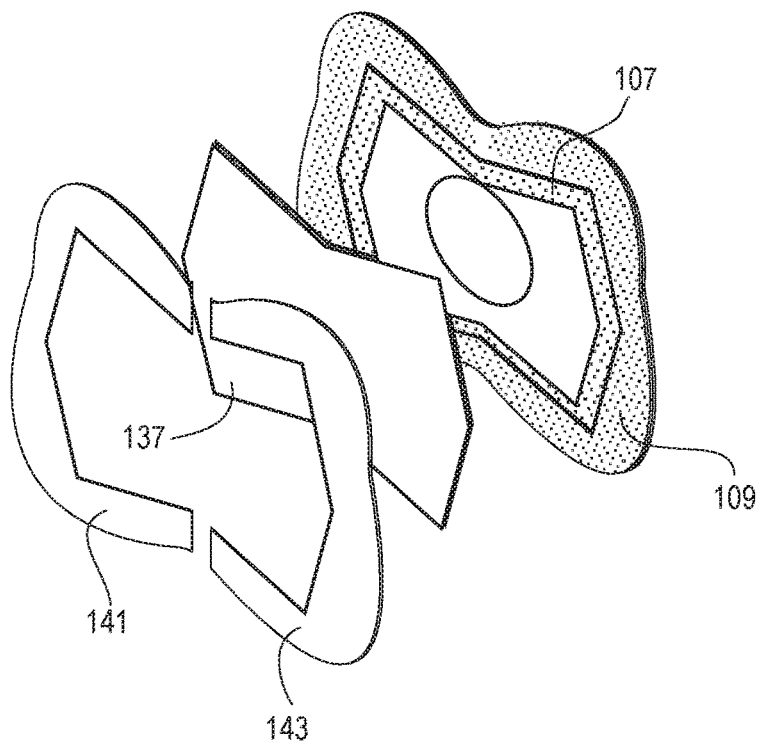
FIG. 4 is an exploded view of the substrate 105 illustrated in FIG. 2.

Additionally, depicted in FIG. 4 is a protective layer. The protective layer covers the substrate 105 before use. In the example depicted in FIG. 4, the protective layer includes two components: a first protective layer 137 and a second protective layer. The first protective layer 137 covers the first adhesive 107 before use. The second protective layer covers the second adhesive 109 before use. In the embodiment depicted in FIG. 4, the second protective layer is made up of two separate pieces: a first protective layer 143 and a second protective layer 141.

The protective layer comprises a material that can be easily removed from the adhesive, such as a coated paper (e.g., wax paper). Accordingly, the protective layer is easily removed from the substrate before and/or during application on the patient.

Figure 6:
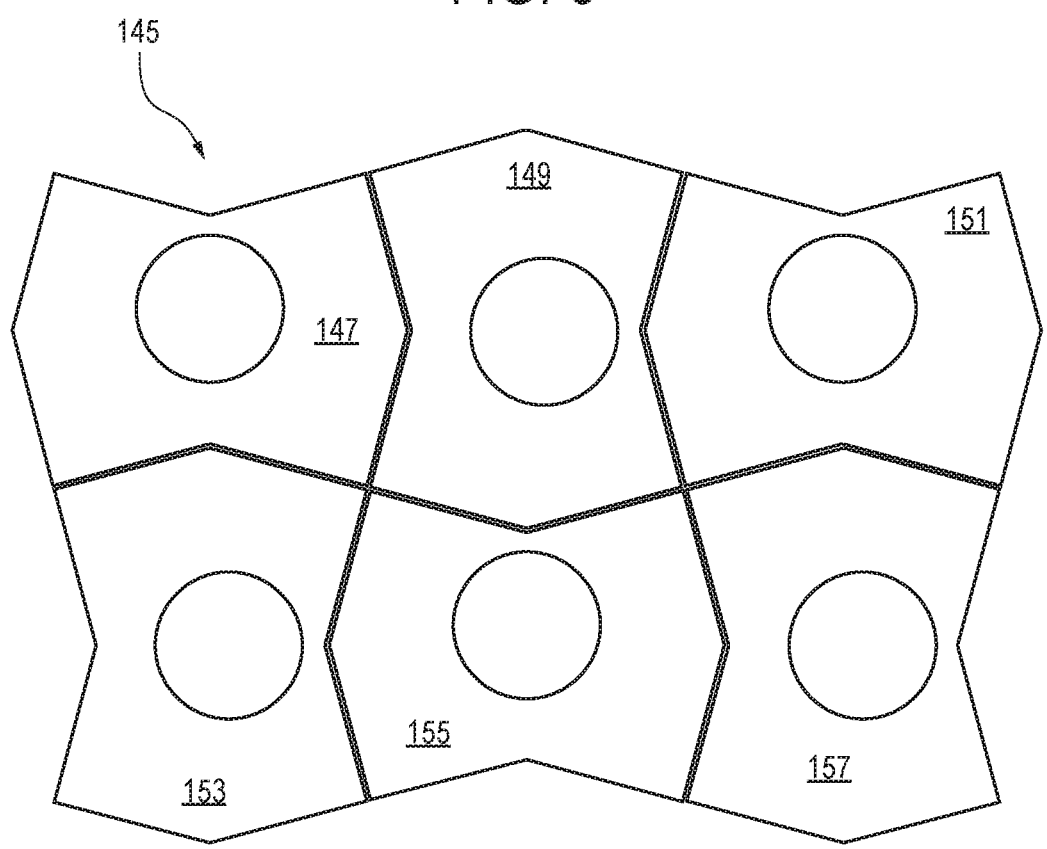
FIG. 6 is a plan view of a first adhesive cutout for a substrate as illustrated in FIG. 2.

The first adhesive cutout 145 depicts an example of the space-saving polygonal shape of the first adhesive. As seen in FIG. 6, in some embodiments, the space-saving polygonal shape can be a tessellating, or near tessellating, shape. The first adhesive cutout 145 includes six pieces of the first adhesive, as indicated by reference numerals 147, 149, 151, 153, 155, and 157. In some embodiments, the first adhesive pieces of the first adhesive cutout 145 are cut from a flat sheet of the adhesive material.

The sheath port 111 is connected to the sheath 103. For example, the sheath port 111 can be connected to the sheath 103 in a traditional sense (i.e., the sheath port 111 is a component separate from the sheath 103) via, for example, a clip, snap fit, heat seal, etc. Alternatively, the sheath port 111 can be connected to the sheath 103 by being integral to the sheath 103 (e.g., the sheath port 111 and sheath 103 can be a single molded piece).

Figure 7:
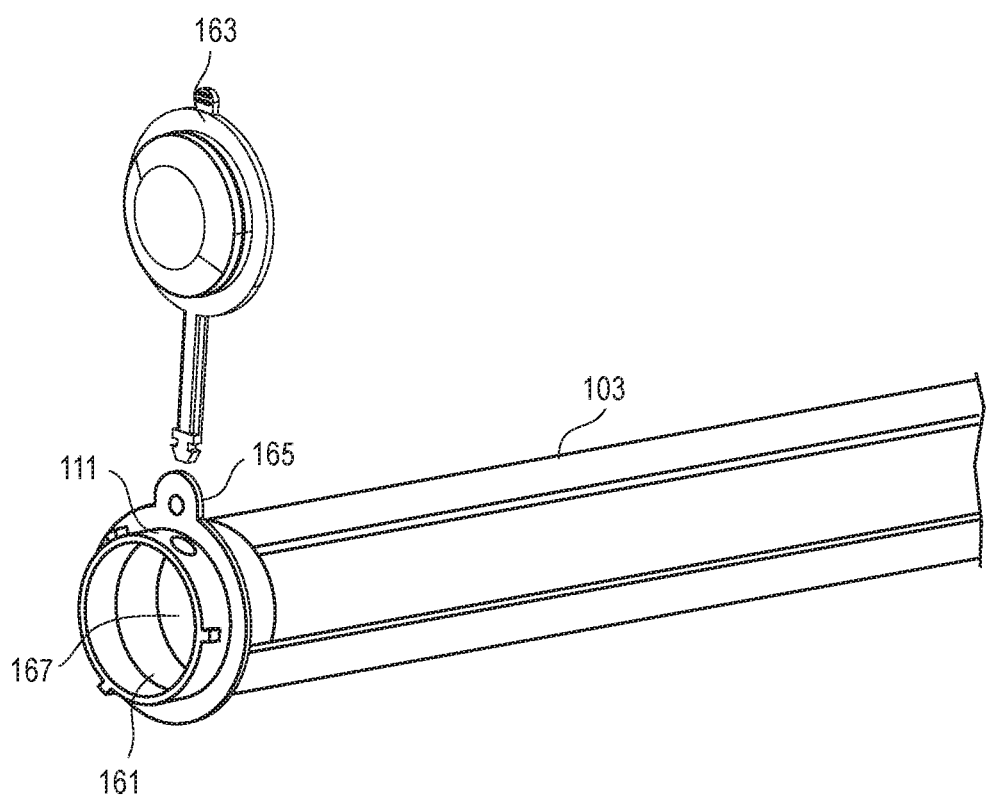
FIG. 7 is a perspective view of a distal end portion of a sheath of a fecal management device, as illustrated in FIG. 1, illustrating a sheath port.
Figure 8:
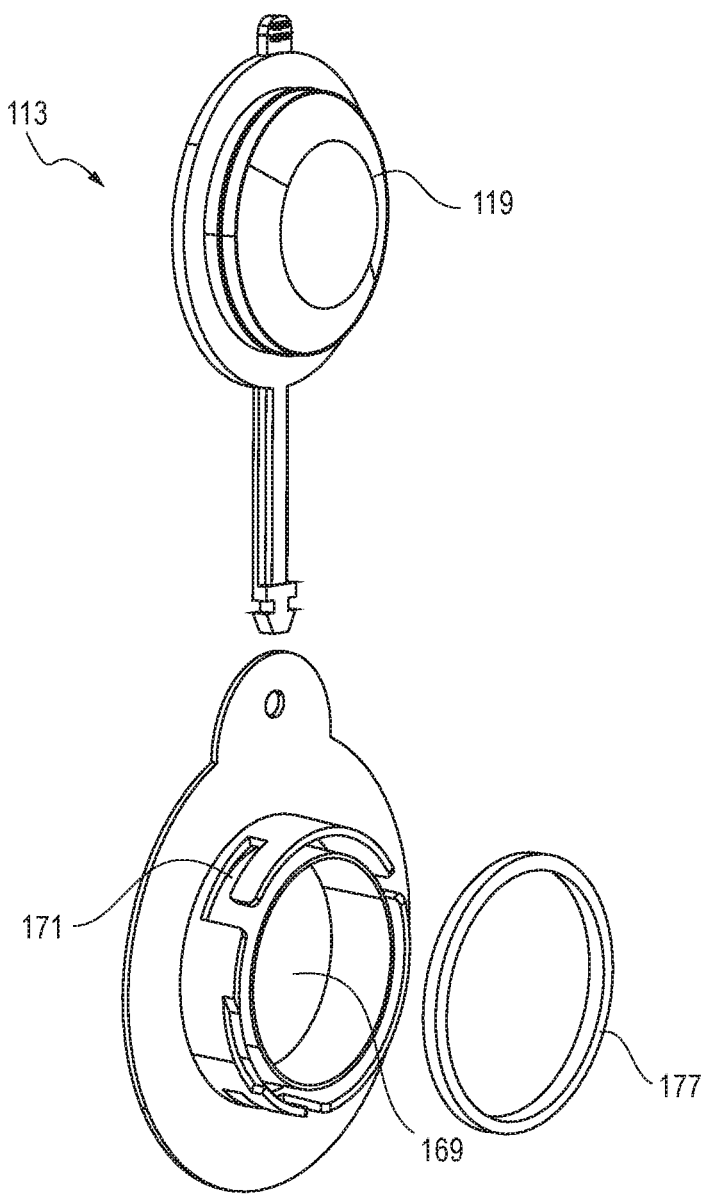
FIG. 8 is a perspective view of a collection bag port of an exemplary collection bag, the collection bag port configured to mate with the sheath port shown in FIG. 7.

The sheath port 111 is configured to mate with a collection bag port, such as the collection bag port 113 depicted in FIG. 8. In this manner, the sheath port 111 allows a collection bag to be quickly and easily removed from the sheath 103. The sheath port 103 can mate with the collection bag port 113 in any suitable connection mechanism (e.g., ball and detent, post and recess, bayonet connector, etc.). In one embodiment, the connector is a quick connect mechanism that allows the collection bag to be quickly and easily removed from the sheath port 111. The quick connect mechanism depicted in FIG. 7 is similarly configured to a bayonet-style connection. This mechanism includes posts 161 spaced radially about the sheath port 111. The posts mate with complementary openings 171 in the collection bag port, as depicted in FIG. 8.

In some embodiments, the sheath port 111 includes a sheath port cap 163. Preferably, the sheath port cap 163 is tethered to the fecal management device. For example, the sheath port cap 163 can be tethered to the sheath port 111 (e.g., via a sheath port cap connector 165) or the sheath 103. The cap is configured to mate with a sheath port opening 167 of the sheath port 111 to prevent unwanted egress of fecal matter from the sheath 103 when the collection bag is removed. The sheath port cap 163 can mate with the sheath port 111 in any suitable manner. For example, as depicted in FIG. 7, the geometry of the sheath port cap 163 can be such that the cap is retained within the sheath port opening 167 of the sheath port 111 due to a tight tolerance. In this example, the sheath port cap 163 can include a portion that is sized slightly smaller than the sheath port opening 167 of the sheath port 111 and/or include pliable material that allows insertion of the sheath port cap 163 in the sheath port opening 167 of the sheath port 111. Alternatively, or additionally, the sheath port cap 163 can include a mating mechanism that is complementary to the sheath port 111.

Figure 9:
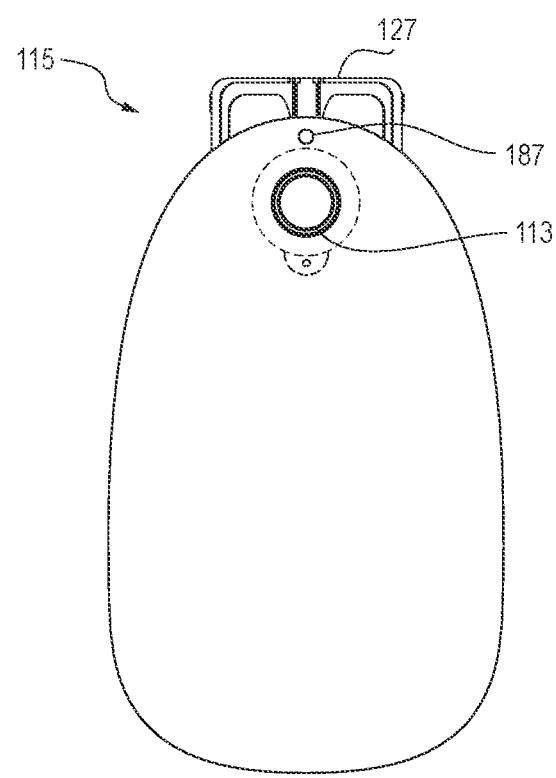
FIG. 9 is a front elevational view of an exemplary collection bag.

The collection bag port 113 is affixed to a collection bag (e.g., a collection bag such as that shown in FIG. 9). The collection bag port 113 allows fecal matter to flow from the sheath into the collection bag via the collection bag port opening 179.

Referring now to FIG. 9, the collection bag port 113 is depicted in FIG. 9 as being located between the first section 121 and second section 123 of the collection bag, as indicated by the dashed lines. The collection bag port 113 protrudes through the first section of the collection bag 115 so as to mate with the sheath port. Though FIG. 9 depicts the collection bag port 113 as being located between the first section 121 and the second section 123 of the collection bag, in some embodiments, the collection bag port 113 is located on an outer surface of the first section 121 of the collection bag 115.

Figure 10:
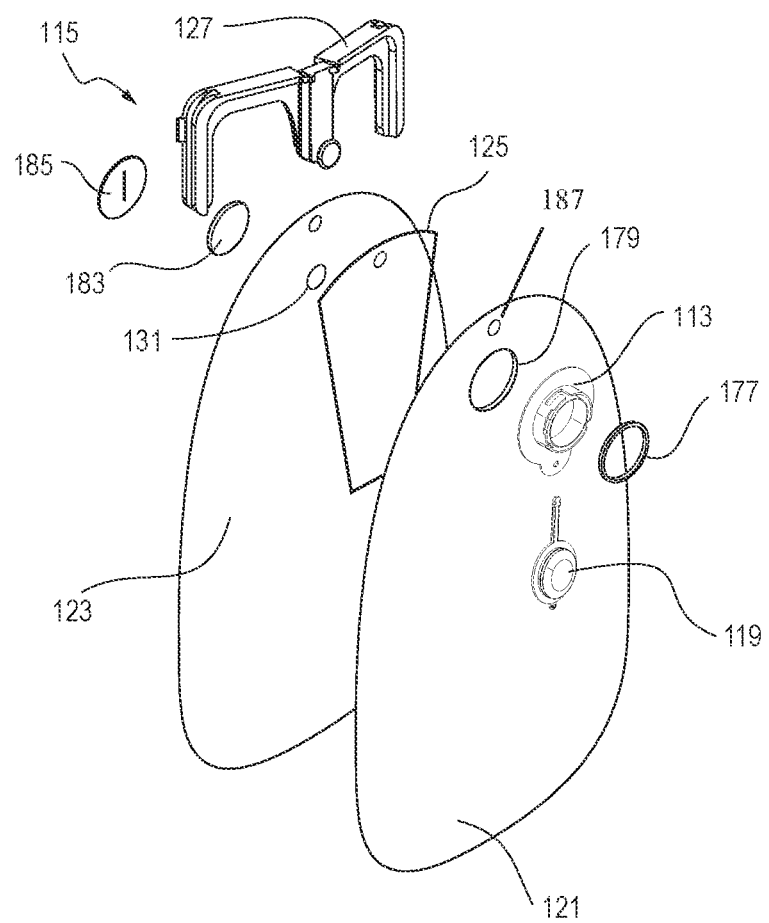
FIG. 10 is an exploded view of the collection bag shown in FIG. 9.

The collection bag 115 depicted in FIG. 10 is but an example and can include a variety of different components and/or capabilities. The example collection bag 115 depicted in FIG. 10 comprises two sections: a first section 121 and a second section 123. The first section 121 and the second section 123 comprise fluid-impermeable plastic and are affixed to one another (e.g., via heat sealing).

The first section 121 includes a collection bag port opening 179. The collection bag port opening 179 allows fecal matter to enter the collection bag 115 via the sheath. A collection bag port 113 is affixed to the collection bag 115 at the collection bag port opening 179. The collection bag port 113 can be affixed to an outer surface of the first section 121 (as depicted in FIG. 10) or affixed to an inner surface of the first section 121 (i.e., between the first section 121 and the second section 123). In embodiments in which the collection bag port 113 is affixed to the outer surface of the first section 121, the collection bag port opening 179 is positioned within a corresponding opening 169 in the collection bag port 113. In embodiments in which the collection bag port 113 is affixed to an inner surface of the first section 121, the collection bag port 113 extends through the collection bag port opening 179. In either case, the collection bag port 113 is configured to mate with a sheath port. In some embodiments, the collection bag port 113 includes a collection bag port cap 119, as discussed in more detail with respect to FIG. 8.

The second section 123 includes a filter port 131. The filter port 131 allows gas to escape from the collection bag 115. The filter port 131 includes a filter 183 (e.g., a charcoal filter) and a filter cover 185. The filter cover 185 is disposed over the filter port 131 and the filter 183 is disposed between the filter cover 185 and the filter port 131.

In the example depicted in FIG. 10, the collection bag 115 includes an anti-reflux device 125. The anti-reflux device 125 prevents, or at least limits, the amount of fecal matter than can escape from the collection bag 115 if the bag is moved or oriented in a different direction (e.g., upside down), as discussed in more detail with respect to FIG. 9. The anti-reflux device 125 is located between the first section 121 and the second section 123 and is affixed to the first section 121 and/or the second section 123.

The example collection bag 115 depicted in FIG. 10 also includes a dual hanger 127. The dual hanger allows the collection bag to be hung from, or otherwise supported by, a structure external to the collection bag 115 (e.g., a bed, rack, stand, hook, etc.). The dual hanger 127 is affixed to the collection bag 115 via a hanger aperture 187. As depicted in FIG. 10, the hanger aperture 187 extends through the first portion 121, the second portion 123, and the anti-reflux device 125. The dual hanger 127 includes a structure 195 that extends through the hanger aperture 187.

Figure 11:
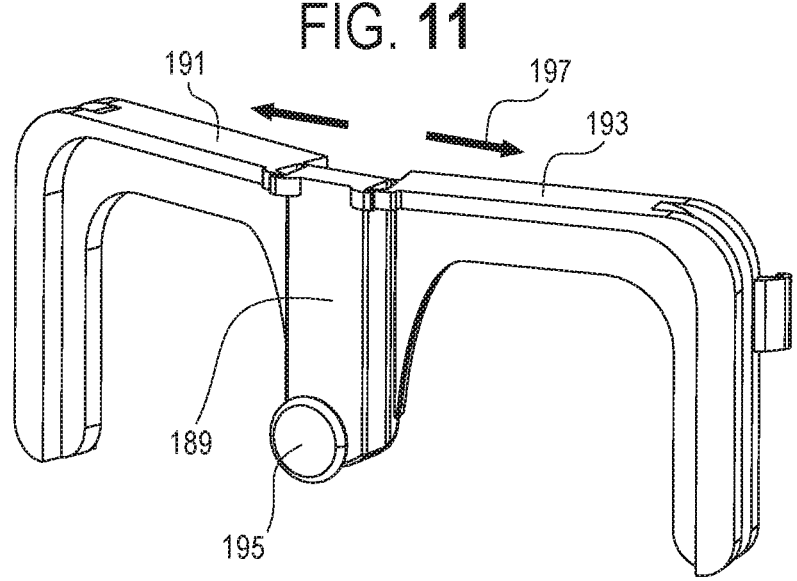
FIG. 11 is a perspective view, relatively enlarged with respect to FIG. 10, of a dual hanger of the illustrated collection bag, showing the dual hanger in a flat wall clasp position.

The dual hanger 127 can comprise any suitable material (e.g., plastic, metal, composite, etc.). The dual hanger 127 includes a central body 189, a first clamp portion 191, and a second clamp portion 193. The first clamp portion 191 and the second clamp portion 193 are operable to hang from a wall clasp, or other structure suited to supporting a collection bag. The dual hanger 127 also includes a structure 195 to secure the dual hanger 127 to the collection bag. The structure 195 can be of any type suitable to secure the dual hanger 127 to the collection bag (e.g., a clamp, clasp, hook, button, snap, etc.). As depicted in FIG. 11, the structure 195 is a shaft with end portion. Accordingly, the structure 195 can extend through an aperture in collection bag 115 to secure the dual hanger 127 to the collection bag, as depicted in FIG. 10.

The first clamp portion 191 is connected to the central body 189 via a first living hinge and the second clamp portion 193 is connected to the central body 189 via a second living hinge. The first and second hinges can be of any type suitable to the composition of the dual hanger (e.g., barrel hinges, spring hinges, etc.). The first and second hinges allow the first clamp portion 191 and the second clamp portion 193, respectively, to pivot about the central body 189. That is, the first clamp portion 191 and the second clamp portion 193 are pivotable about the central body 189 over a range of travel, as depicted by arrow 197. In one embodiment, the first and second hinges allow the first clamp portion 191 and the second clamp portion 193 to pivot between a flat wall clasp position (depicted in FIG. 11) and a frame hook position (depicted in FIG. 12).

Figure 12:
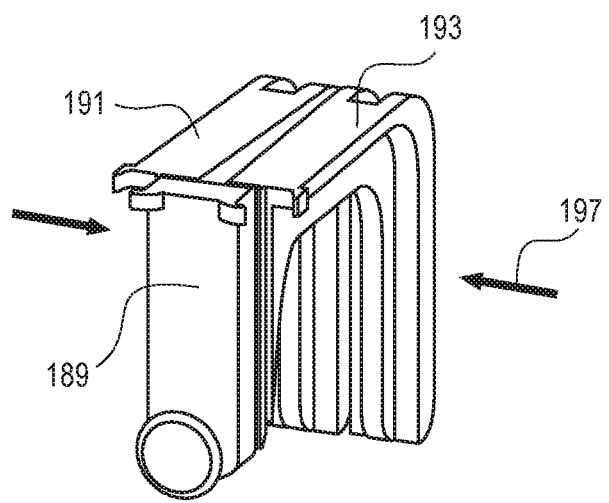
FIG. 12 is a perspective view of the dual hanger shown in FIG. 11, showing the dual hanger in a frame hook position.

In FIG. 12, the dual hanger 127 has been manipulated from the wall clasp position to the frame hook position, as indicated by arrow 197. The first clamp portion 191 and the second clamp portion 193 have been rotated about the central body 189 via a first and second hinge. The first hinge connects the first clamp portion 191 to the central body 189 and the second hinge connects the second clamp portion 193 to the central body 189.

It is thus seen that a fecal management system is provided.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A fecal management device comprising:
   a sheath having a first end and a second end;
   a first connector at the first end of the sheath, said first connector comprising a substrate that includes a first adhesive and a second adhesive, the second adhesive disposed relatively outwardly with respect to the first adhesive, the substrate having a multi-lobed contour with two opposing convex regions and two opposing concave regions, the first adhesive being disposed on a secondary substrate, and the second adhesive has a central aperture greater than a central aperture of the first adhesive;

a sheath port located at the second end of the sheath, the sheath port configured to removably mate with a collection bag port; and a collection bag, wherein the collection bag includes the collection bag port.

2. The fecal management device of claim 1, wherein the secondary substrate has the shape of a tessellating or near tessellating space-filling polygon.

3. The fecal management device of claim 1, wherein the first adhesive is a hydrocolloid adhesive.

4. The fecal management device of claim 1, the collection bag including an anti-reflux device.

5. The fecal management device of claim 1, the collection bag including a filter port.

6. The fecal management device of claim 1, the collection bag including a dual hanger, the dual hanger comprising a central body connected via a first living hinge to a first clamp portion and connected via a second living hinge to a second clamp portion, the first and second clamp portions being pivotable over a range of travel between a frame hook position and a flat wall clasp position.

7. The fecal management device of claim 1, wherein the collection bag includes a cap, and wherein the cap is configured to mate with the collection bag port.

8. A method comprising applying the fecal management device of claim 1 to a patient, removing said collection bag after said patient excretes fecal matter into said fecal management device, and replacing said collection bag with a second collection bag, said second collection bag having a collection bag port configured to mate with the sheath port.

9. The method of claim 8, wherein the secondary substrate has the shape of a space-filling polygon.

10. The method of claim 8, wherein the first adhesive is a hydrocolloid adhesive.

11. The method of claim 8, the collection bag including an anti-reflux device.

12. The method of claim 8, the collection bag including a filter port.

13. The method of claim 8, the collection bag including a dual hanger, the dual hanger comprising a central body connected via a first living hinge to a first clamp portion and connected via a second living hinge to a second clamp portion, the first and second clamp portions being pivotable over a range of travel between a frame hook position and a flat wall clasp position.

14. The method of claim 8, wherein the collection bag includes a cap, and wherein the cap is configured to mate with the collection bag port.

15. A fecal management device comprising:
a sheath having a first end and a second end;
a first connector at the first end of the sheath, said first connector comprising a substrate that includes at least one adhesive, the substrate having a multi-lobed contour with two opposing convex regions and two opposing concave regions;
a sheath port located at the second end of the sheath, the sheath port configured to removably mate with a collection bag port; and
a collection bag, wherein the collection bag includes the collection bag port, the at least one adhesive including a first adhesive and a second adhesive at least partially covering the first adhesive and having a central aperture larger than a central aperture of the first adhesive.

16. The fecal management device of claim 15, wherein at least one of the first adhesive and the second adhesive is a hydrocolloid adhesive.

17. The fecal management device of claim 15, the substrate including an aperture.

18. The fecal management device of claim 15, the collection bag including a dual hanger, the dual hanger comprising a central body connected via a first living hinge to a first clamp portion and connected via a second living hinge to a second clamp portion, the first and second clamp portions being pivotable over a range of travel between a frame hook position and a flat wall clasp position.

19. The fecal management device of claim 15, the collection bag including a filter port and an anti-reflux device that is disposed between the collection bag port and the filter port.

* * * * *